United States Patent
Zhang

(10) Patent No.: US 9,816,426 B2
(45) Date of Patent: Nov. 14, 2017

(54) SYSTEM FOR SENSING PARTICULATE MATTER

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 102 days.

(21) Appl. No.: 14/852,338

(22) Filed: Sep. 11, 2015

(65) Prior Publication Data

US 2017/0074148 A1    Mar. 16, 2017

(51) Int. Cl.

| | |
|---|---|
| *F01N 13/00* | (2010.01) |
| *F01N 13/08* | (2010.01) |
| *F01N 3/027* | (2006.01) |
| *F01N 3/033* | (2006.01) |
| *F01N 11/00* | (2006.01) |
| *G01N 15/06* | (2006.01) |
| *F01N 9/00* | (2006.01) |
| *G01N 15/00* | (2006.01) |

(52) U.S. Cl.
CPC .......... *F01N 13/008* (2013.01); *F01N 3/027* (2013.01); *F01N 3/033* (2013.01); *F01N 11/00* (2013.01); *G01N 15/0606* (2013.01); *G01N 15/0656* (2013.01); *F01N 9/002* (2013.01); *F01N 2560/05* (2013.01); *F01N 2900/1606* (2013.01); *F02D 2200/0812* (2013.01); *G01N 2015/0046* (2013.01); *Y02T 10/47* (2013.01)

(58) Field of Classification Search
CPC .......... F01N 3/027; F01N 3/033; F01N 9/002; F01N 2560/05; F01N 2560/20; F01N 2900/1606; F01N 11/00; F01N 13/008; F02D 2200/0812; Y02T 10/47; G01N 15/0606; G01N 15/0656; G01N 2015/0046

See application file for complete search history.

(56) References Cited

U.S. PATENT DOCUMENTS

| | | | |
|---|---|---|---|
| 5,156,658 A | 10/1992 | Riehl | |
| 8,225,648 B2 * | 7/2012 | Nelson | G01N 15/0656 73/114.71 |
| 8,341,936 B2 | 1/2013 | Zhang | |
| 2009/0056416 A1 * | 3/2009 | Nair | G01N 15/0656 73/28.01 |
| 2012/0125081 A1 * | 5/2012 | Yadav | F01N 11/00 73/23.33 |

OTHER PUBLICATIONS

Leone, Thomas G., "Method and System for Secondary Air Injection Coordination With Exhaust Back Pressure Valve," U.S. Appl. No. 14/312,323, filed Jun. 23, 2014, 34 pages.
Zhang, Xiaogang, "System for Sensing Particulate Matter," U.S. Appl. No. 14/299,885, filed Jun. 9, 2014, 49 pages.

(Continued)

*Primary Examiner* — Brandon Lee
(74) *Attorney, Agent, or Firm* — Julia Voutyras; McCoy Russell LLP

(57) ABSTRACT

Systems and methods are described for sensing particulate matter in an exhaust system of a vehicle. An example system comprises a particulate matter sensor and a guiding plate spaced away from each other in a tube capable of receiving a portion of exhaust gas in an exhaust passage.

18 Claims, 6 Drawing Sheets

(56) References Cited

OTHER PUBLICATIONS

Zhang, Xiaogang, et al. "System for Sensing Particulate Matter," U.S. Appl. No. 14/624,228, filed Feb. 17, 2015, 78 pages.
Yi, Jianwen James et al., "Systems and Methods for Sensing Particulate Matter," U.S. Appl. No. 14/842,573, filed Sep. 1, 2015, 41 pages.
Zhang, Xiaogang, "Exhaust Gas Mixer," U.S. Appl. No. 14/823,700, filed Aug. 11, 2015, 47 pages.

* cited by examiner

SYSTEM FOR SENSING PARTICULATE MATTER

FIELD

The present description relates generally to methods and systems for sensing particulate matter in an exhaust system.

BACKGROUND/SUMMARY

Engine emission control systems may utilize various exhaust sensors. One example sensor may be a particulate matter sensor which indicates particulate matter mass and/or concentration in the exhaust gas. In one example, the particulate matter sensor may operate by accumulating particulate matter over time and providing an indication of the degree of accumulation as a measure of exhaust particulate matter levels.

Particulate matter sensors may encounter problems with non-uniform deposition of soot on the sensor due to a bias in flow distribution across the surface of the sensor. Further, particulate matter sensors may be prone to contamination from an impingement of water droplets and/or larger particulates present in the exhaust gases. This contamination may lead to errors in sensor output. Furthermore, sensor regeneration may be inadequate when a substantial volume of exhaust gases stream across the particulate matter sensor.

The inventors herein have recognized the above issues and identified an approach to at least partly address the issues. In one example approach, a system for sensing particulate matter in an exhaust passage of an engine is provided. The system comprises a tube positioned in an exhaust passage of an engine, a particulate matter sensor positioned within the tube, and a flow guiding plate positioned within the tube substantially parallel to a vertical axis of the tube. The guiding plate comprises a plurality of projections with surfaces of the projections defining an interior passage in proximity to the particulate matter sensor, the surfaces of the projections directing flow against the particulate matter sensor.

As one example, a particulate matter (PM) sensor may be disposed within a tube fixed to a wall of an exhaust passage. The tube may further comprise a flow guiding plate located downstream of the PM sensor. The PM sensor may comprise an electric circuit on an upstream surface directed away from the guiding plate. The PM sensor may further comprise two separate electrodes located on a downstream surface. An interior passage (e.g., a central chamber) may be located between the PM sensor and guiding plate. A sample of exhaust gas may enter the tube via an inlet located on a bottom portion of the tube. Larger particulates and/or water droplets may flow through a drainage hole directly downstream of the inlet on the bottom portion of the tube. The sample of exhaust gas may be conducted up along an outside of the guiding plate before flowing down into the central chamber The sample of exhaust gas flows through guides of the guiding plate and may be evenly distributed across the downstream surface of the PM sensor. Finally, the sample of exhaust gas may exit the tube and flow into the exhaust passage via outlets located at an interface between the guiding plate and the tube.

In this way, a PM sensor may be exposed to a more uniform flow distribution across its surface. By flowing the sample of exhaust gas from a lower portion of the tube to a higher portion of the tube, a flow rate and/or volume of exhaust gas entering the central chamber may be controlled. Further, distribution of particulate matter from the sample of exhaust gas onto the PM sensor may be more evenly distributed due to the guiding plate, which may mix and guide exhaust flow across a total surface area of the downstream surface of the PM sensor. By providing a more even and controlled flow of the sample exhaust gas onto the downstream surface, particulate filter regeneration and/or determination of degradation of the PF in the exhaust passage may occur more accurately. Further, the PM sensor may be protected from larger particulates and water droplets, as they may flow through the drainage hole due to their greater momentum. Overall, functioning of the PM sensor may be improved and may be more reliable.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 2 and 4 are shown approximately to scale.

DETAILED DESCRIPTION

Figure 1:
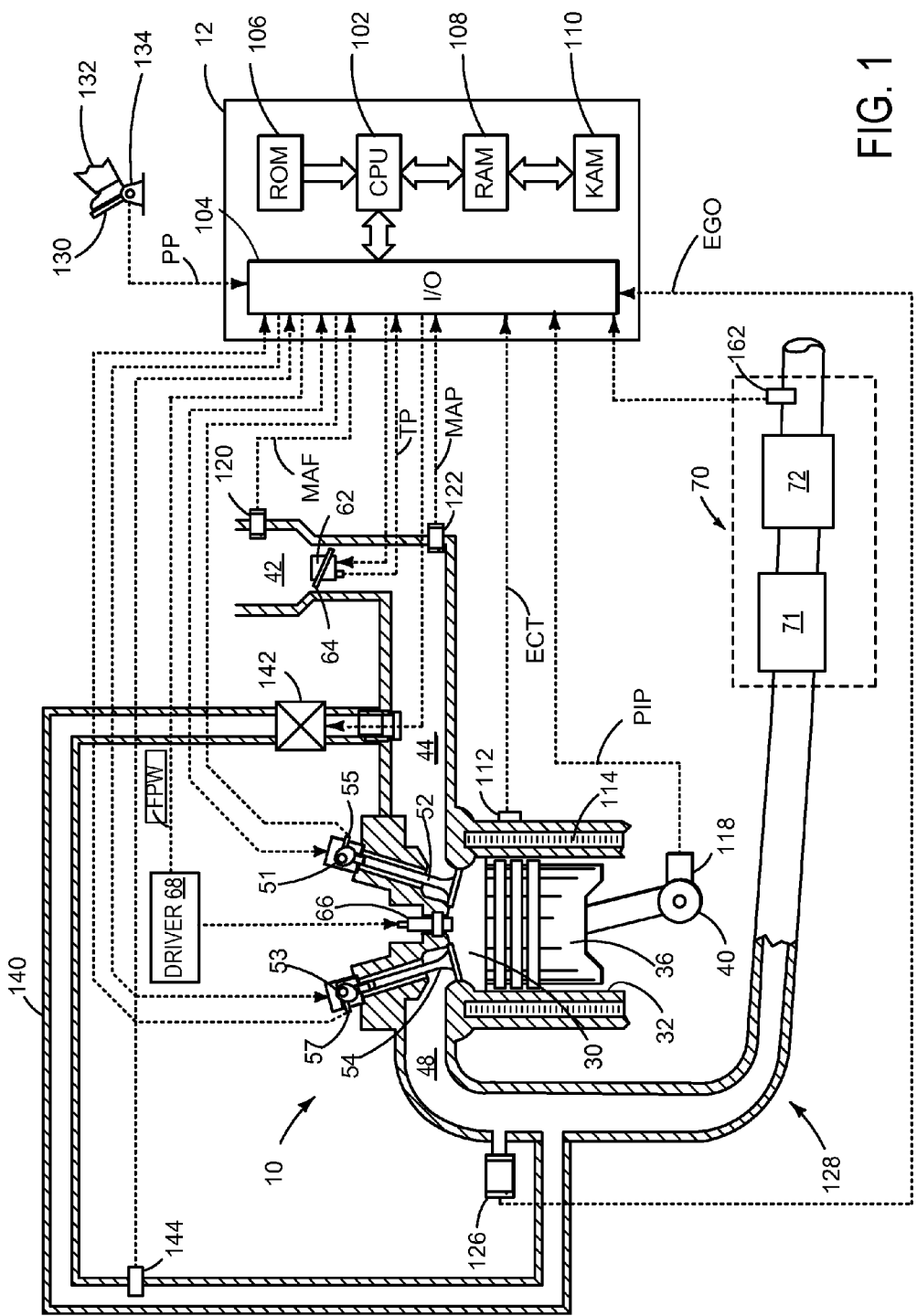
FIG. 1 is a schematic diagram of an engine.
Figure 2:
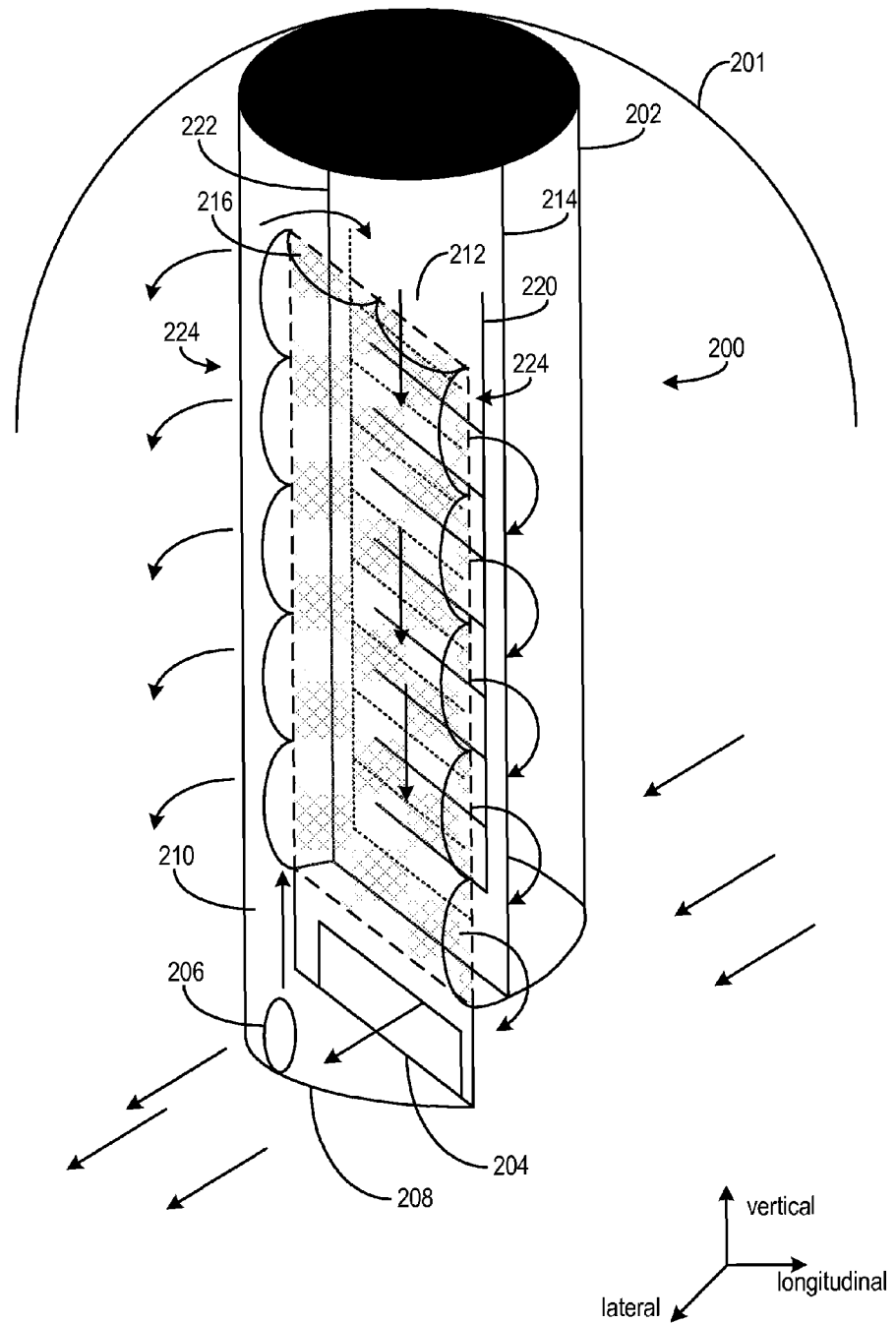
FIG. 2 shows a schematic illustration of a particulate matter (PM) sensor assembly.
Figure 3:
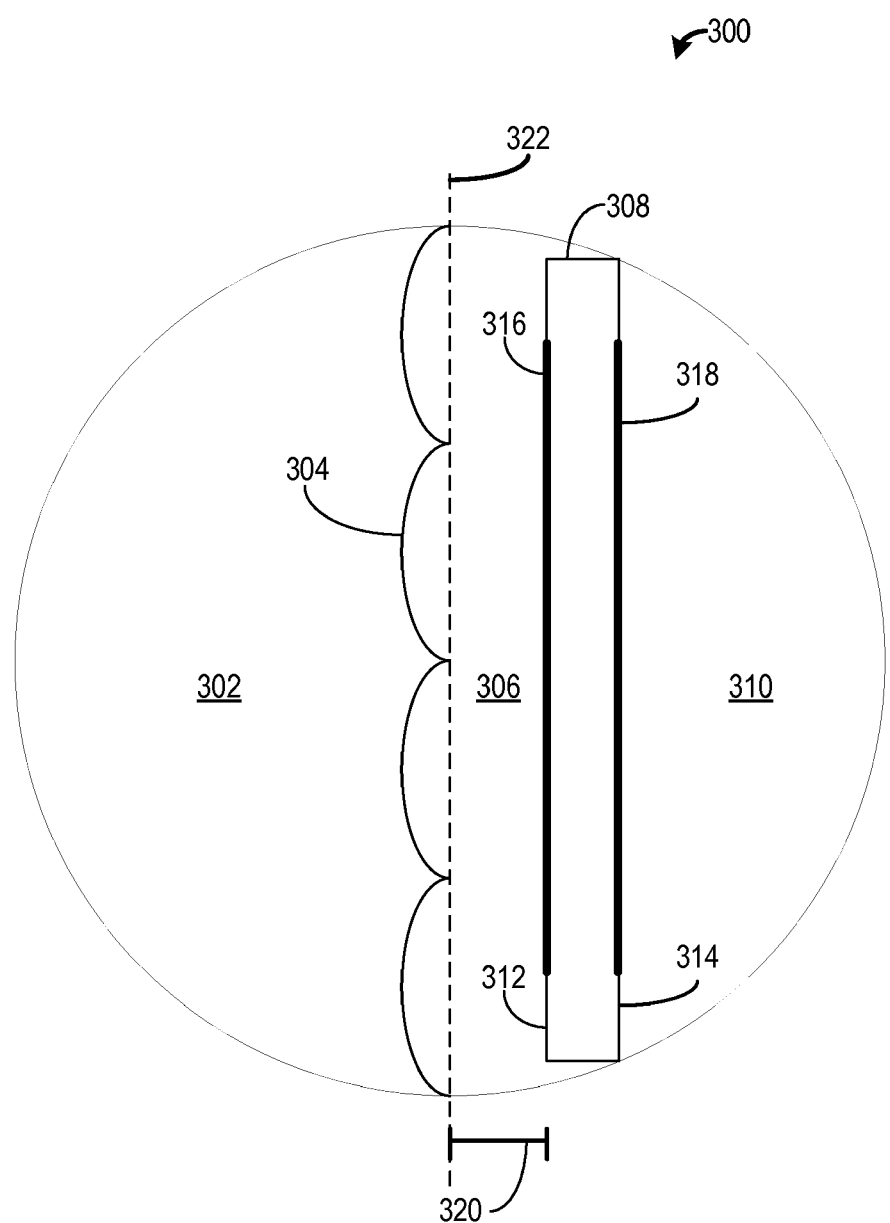
FIG. 3 shows a top-view of the PM sensor assembly.
Figure 4:
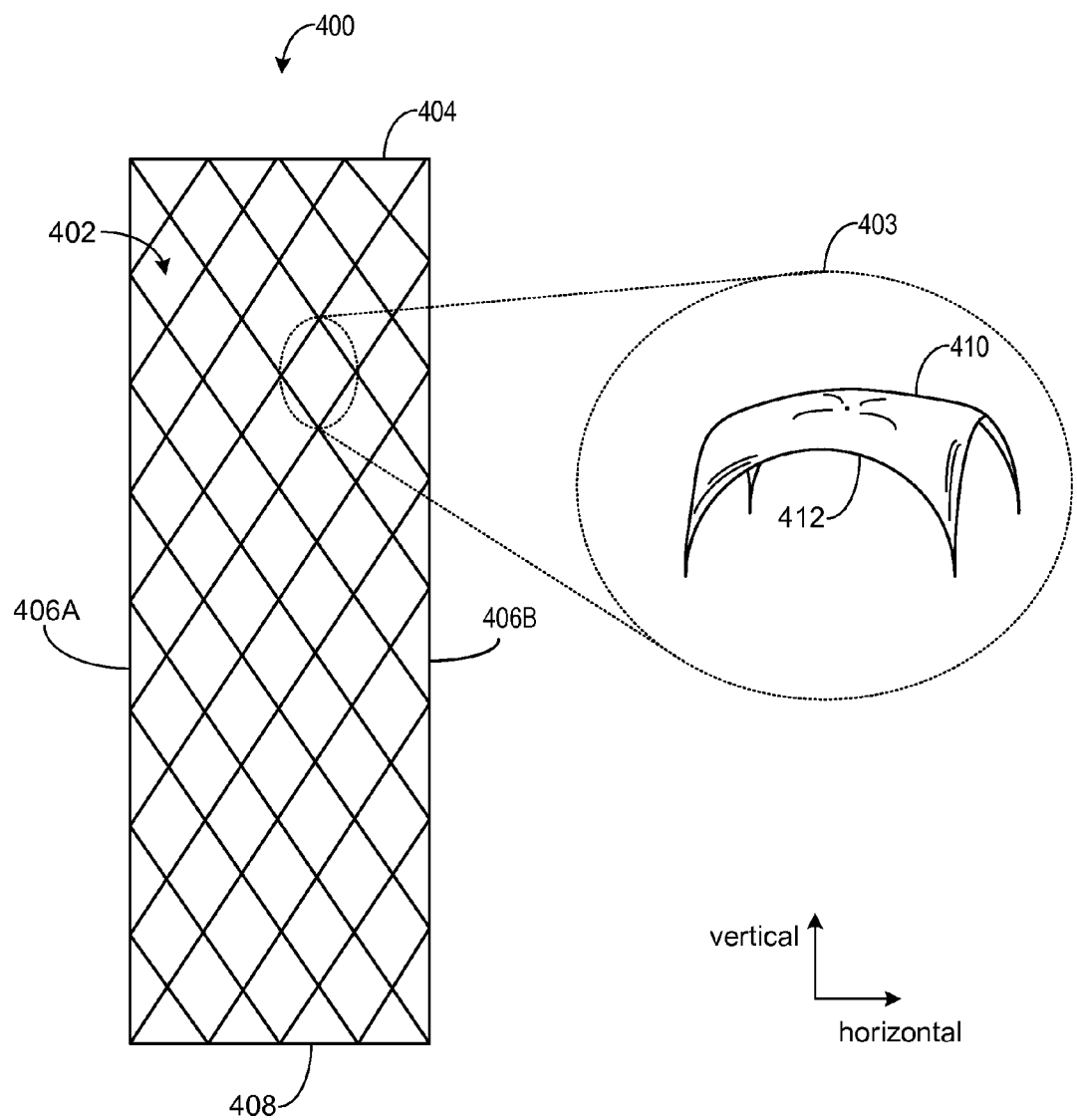
FIG. 4 shows a close-up view of an individual projection of the PM sensor assembly.
Figures 5A, 5B:
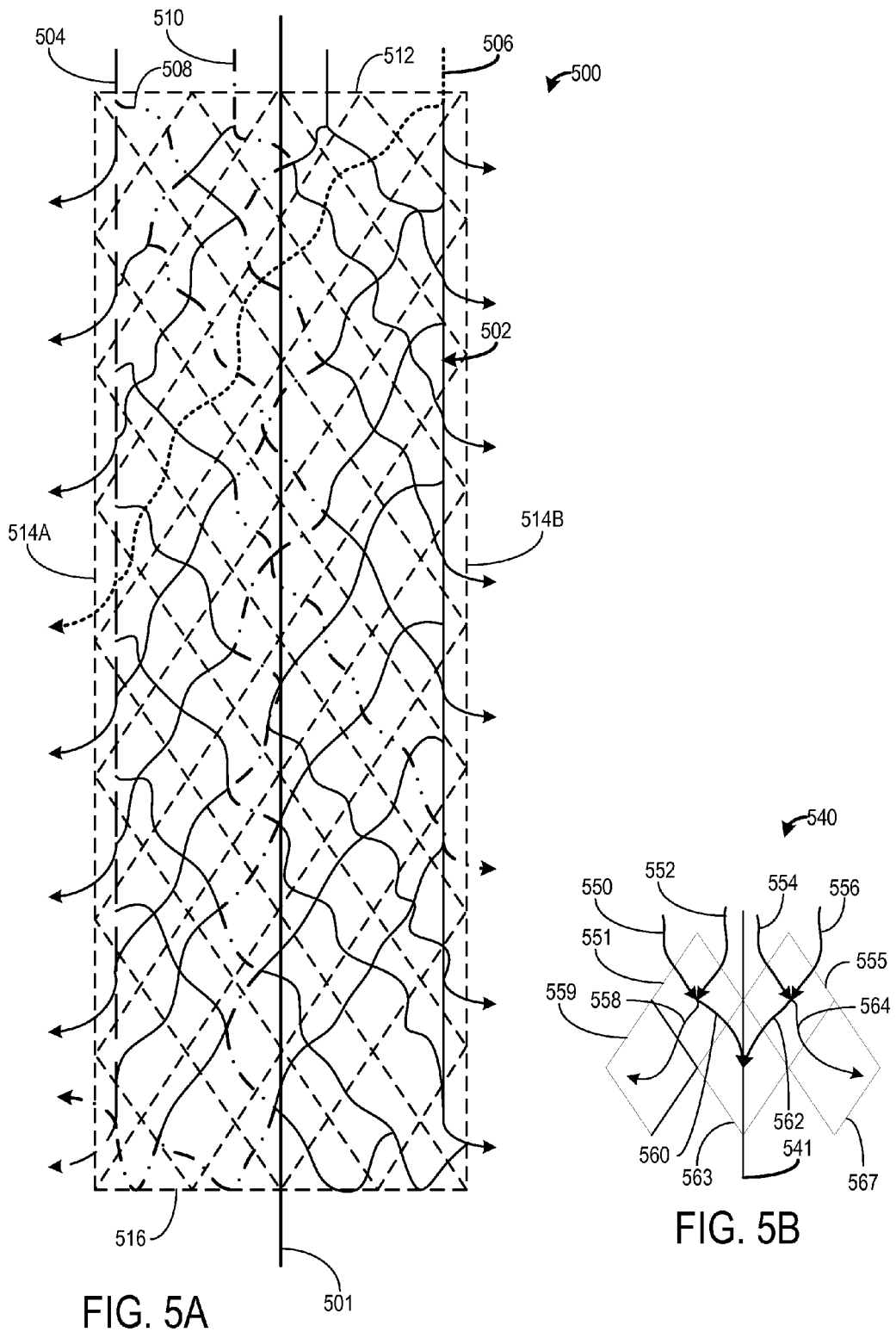
FIG. 5A shows an example exhaust flow through the PM sensor assembly.
FIG. 5B shows a detailed exhaust flow through the projection of the PM sensor assembly.
Figure 6:
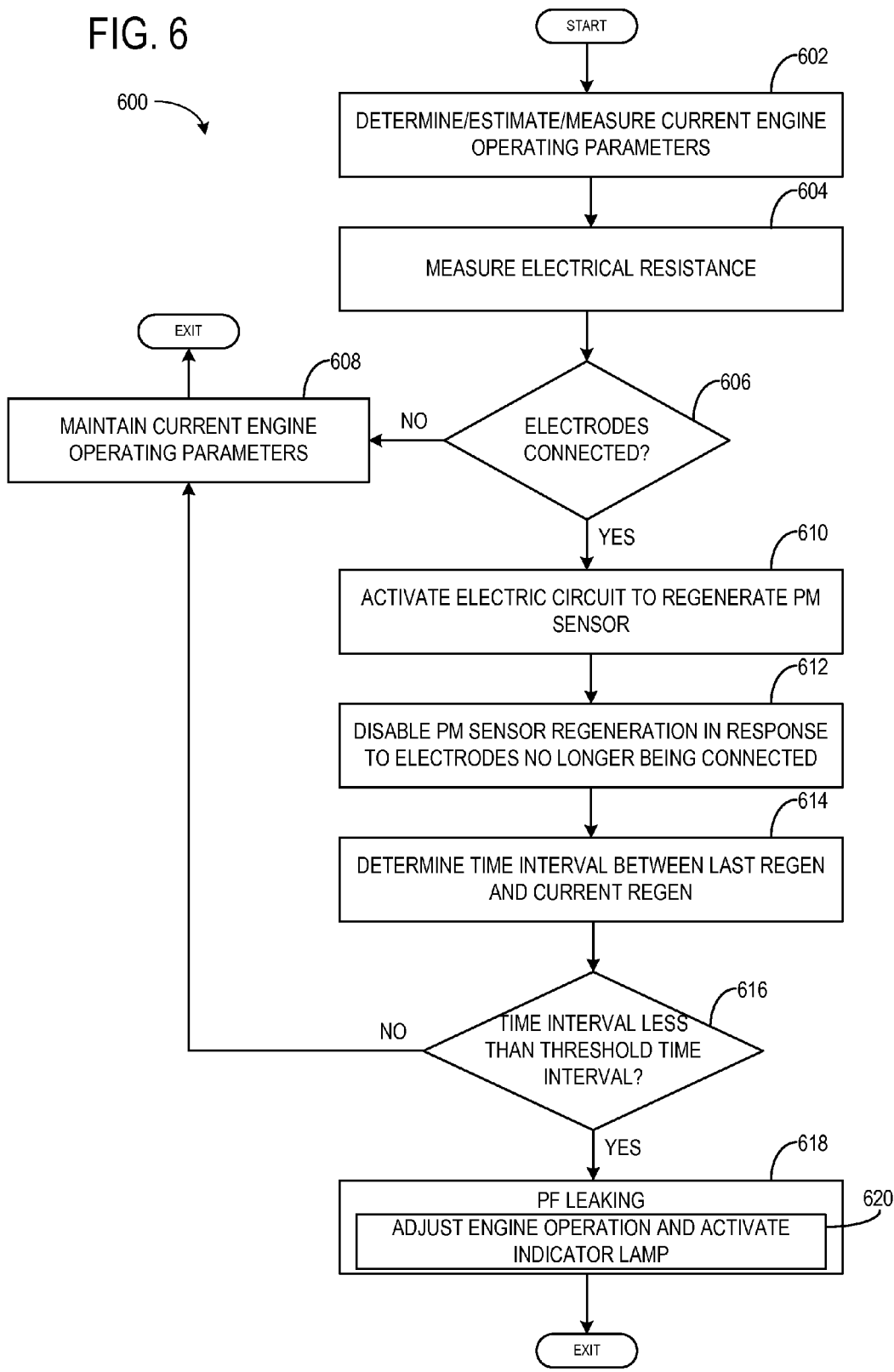
FIG. 6 shows a method for determining if a particulate filter demands a regeneration or is degraded.

The following description relates to systems and methods for sensing particulate matter (PM) in an exhaust flow on an engine system, such as the engine system, as shown in FIG. 1. A PM sensor assembly may include a tube with an inlet on an extension of the tube for receiving a sample exhaust flow and a drainage hole opposite the inlet on the extension, as shown in FIG. 2. An outer chamber may guide the sample exhaust flow up the tube toward a central chamber located between a PM sensor and a guiding plate, as shown in FIG. 3. The tube may further include a PM sensor located upstream of a guiding plate. The guiding plate may comprise a plurality of concave projections, protruding away from the PM sensor, as shown in FIG. 4. The guiding plate may control an exhaust flow similar to a quincunx (e.g., Galton box) and evenly distribute an exhaust flow across a surface of the PM sensor, as shown in FIGS. 5A and 5B. A method for determining if a particulate matter load of a particulate filter is greater than a threshold particulate load and if the particulate filter is degraded, as shown in FIG. 6.

FIGS. 1-5B show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example.

Referring now to FIG. 1, it shows a schematic diagram with one cylinder of multi-cylinder engine 10, which may be included in a propulsion system of a vehicle. Engine 10 may be controlled at least partially by a control system including a controller 12 and by input from a vehicle operator 132 via an input device 130. In this example, input device 130 includes an accelerator pedal and a pedal position sensor 134 for generating a proportional pedal position signal PP. A combustion chamber 30 (also termed, cylinder 30) of the engine 10 may include combustion chamber walls 32 with a piston 36 positioned therein. Piston 36 may be coupled to a crankshaft 40 so that reciprocating motion of the piston is translated into rotational motion of the crankshaft 40. Crankshaft 40 may be coupled to at least one drive wheel (not shown) of a vehicle via an intermediate transmission system (not shown). Further, a starter motor (not shown) may be coupled to the crankshaft 40 via a flywheel (not shown) to enable a starting operation of the engine 10.

Combustion chamber 30 may receive intake air from an intake manifold 44 via an intake passage 42 and may exhaust combustion gases via an exhaust passage 48. The intake manifold 44 and the exhaust passage 48 can selectively communicate with the combustion chamber 30 via intake valve 52 and exhaust valve 54 respectively. In some embodiments, the combustion chamber 30 may include two or more intake valves and/or two or more exhaust valves.

In the example depicted in FIG. 1, the intake valve 52 and exhaust valve 54 may be controlled by cam actuation via respective cam actuation systems 51 and 53. The cam actuation systems 51 and 53 may each include one or more cams and may utilize one or more of cam profile switching (CPS), variable cam timing (VCT), variable valve timing (VVT), and/or variable valve lift (VVL) systems that may be operated by the controller 12 to vary valve operation. The position of the intake valve 52 and the exhaust valve 54 may be determined by position sensors 55 and 57, respectively. In alternative embodiments, the intake valve 52 and/or exhaust valve 54 may be controlled by electric valve actuation. For example, the cylinder 30 may alternatively include an intake valve controlled via electric valve actuation and an exhaust valve controlled via cam actuation including CPS and/or VCT systems.

In some embodiments, each cylinder of the engine 10 may be configured with one or more fuel injectors for providing fuel thereto. As a non-limiting example, the cylinder 30 is shown including one fuel injector 66. Fuel injector 66 is shown coupled to the cylinder 30 for injecting fuel directly therein in proportion to the pulse width of signal FPW received from controller 12 via electronic driver 68. In this manner, fuel injector 66 provides what is known as direct injection of fuel into combustion chamber 30. It will also be appreciated that the cylinder 30 may receive fuel from a plurality of injections during a combustion cycle. In other examples, the fuel injector may be mounted in the side of the combustion chamber or in the top of the combustion chamber, for example. Fuel may be delivered to fuel injector 66 by a fuel system (not shown) including a fuel tank, a fuel pump, and a fuel rail.

In the example shown in FIG. 1, engine 10 is configured as a diesel engine that combusts air and diesel fuel through compression ignition. In other embodiments, the engine 10 may combust a different fuel including gasoline, biodiesel, or an alcohol containing fuel blend (e.g., gasoline and ethanol, or gasoline and methanol) through compression ignition and/or spark ignition. Thus, the embodiments described herein may be used in any suitable engine, including but not limited to, diesel and gasoline compression ignition engines, spark ignition engines, direct or port injection engines, etc.

The intake passage 42 may include a throttle 62 having a throttle plate 64. In this particular example, the position of the throttle plate 64 may be varied by controller 12 via a signal provided to an electric motor or actuator included with the throttle 62, a configuration that is commonly referred to as electronic throttle control (ETC). In this manner, the throttle 62 may be operated to vary the intake air provided to the combustion chamber 30 among other engine cylinders. The position of the throttle plate 64 may be provided to the controller 12 by throttle position signal TP. The intake passage 42 may include a mass air flow sensor 120 and a manifold air pressure sensor 122 for providing respective signals MAF and MAP to the controller 12.

Further, in the disclosed embodiments, an exhaust gas recirculation (EGR) system may route a desired portion of exhaust gas from the exhaust passage 48 to the intake manifold 44 via an EGR passage 140. An amount of EGR provided may be varied by controller 12 via an EGR valve 142. By introducing exhaust gas to the engine 10, the amount of available oxygen for combustion is decreased, thereby reducing combustion flame temperatures and reducing the formation of NOx, for example. As depicted, the EGR system further includes an EGR sensor 144 which may be arranged within the EGR passage 140 and may provide an indication of one or more of pressure, temperature, and concentration of the exhaust gas. Under some conditions, the EGR system may be used to regulate the temperature of the air and fuel mixture within the combustion chamber 30, thus providing a method of controlling the timing of ignition during some combustion modes. Further, during some conditions, a portion of combustion gases may be retained or trapped in the combustion chamber by controlling exhaust valve timing, such as by controlling a variable valve timing mechanism.

An exhaust system 128 includes an exhaust gas sensor 126 coupled to the exhaust passage 48 upstream of an emission control system 70 and the EGR passage 140. Exhaust gas sensor 126 may be any suitable sensor for providing an indication of exhaust gas air/fuel ratio such as a linear oxygen sensor or UEGO (universal or wide-range exhaust gas oxygen), a two-state oxygen sensor or EGO, a HEGO (heated EGO), NOx, HC, or CO sensor.

Emission control system 70 is shown arranged along exhaust passage 48 downstream of exhaust gas sensor 126. Emission control system 70 may be a selective catalytic reduction (SCR) system, three way catalyst (TWC), NOx trap, various other emission control devices, or combinations thereof. For example, emission control system 70 may include an SCR catalyst 71 and a particulate filter (PF) 72. In some embodiments, PF 72 may be located downstream of the SCR catalyst 71 (as shown in FIG. 1), while in other embodiments, PF 72 may be positioned upstream of the SCR catalyst 71 (not shown in FIG. 1). Emission control system 70 may further include exhaust gas sensor 162. Sensor 162 may be any suitable sensor for providing an indication of a concentration of exhaust gas constituents such as a NOx, NH3, EGO, or a particulate matter (PM) sensor, for example. In some embodiments sensor 162 may be located downstream of PF 72 (as shown in FIG. 1), while in other embodiments, sensor 162 may be positioned upstream of PF 72 (not shown in FIG. 1). Further, it will be appreciated that more than one sensor 162 may be provided in any suitable position.

As described in more detail with reference to FIG. 2, sensor 162 may be a PM sensor assembly comprising a PM sensor and may measure the mass or concentration of particulate matter downstream of PF 72. For example, sensor 162 may be a soot sensor. Sensor 162 may be operatively coupled to controller 12 and may communicate with controller 12 to indicate a concentration of particulate matter within exhaust exiting PF 72 and flowing through exhaust passage 48. In this way, sensor 162 may detect leakages from PF 72.

Further, in some embodiments, during operation of engine 10, emission control system 70 may be periodically reset by operating at least one cylinder of the engine within a particular air/fuel ratio.

Controller 12 is shown in FIG. 1 as a microcomputer, including a microprocessor unit 102, input/output ports 104, an electronic storage medium for executable programs and calibration values shown as a read only memory chip 106 in this particular example, random access memory 108, keep alive memory 110, and a data bus. The controller 12 may be in communication with and, therefore, receive various signals from sensors coupled to the engine 10, in addition to those signals previously discussed, including measurement of inducted mass air flow (MAF) from the mass air flow sensor 120; engine coolant temperature (ECT) from a temperature sensor 112 coupled to a cooling sleeve 114; a profile ignition pickup signal (PIP) from a Hall effect sensor 118 (or other type) coupled to the crankshaft 40; throttle position (TP) from a throttle position sensor; absolute manifold pressure signal, MAP, from the sensor 122; and exhaust constituent concentration from the exhaust gas sensor 126. Engine speed signal, RPM, may be generated by controller 12 from signal PIP.

The controller 12 receives signals from the various sensors of FIG. 1 (e.g., exhaust gas sensor 162) and employs the various actuators of FIG. 1 to adjust engine operation based on the received signals and instructions stored on a memory of the controller.

As described above, FIG. 1 shows only one cylinder of a multi-cylinder engine, and each cylinder may similarly include its own set of intake/exhaust valves, fuel injector(s), spark plug(s), etc.

Turning now to FIG. 2, a schematic view of an example embodiment of a PM sensor assembly 200 is shown. PM sensor assembly 200 may be used as exhaust gas sensor 162 of FIG. 1 and therefore may share common features and/or configurations as those already described for exhaust gas sensor 162. PM sensor assembly 200 may be configured to measure PM mass and/or concentration in the exhaust gas, and as such, may be coupled to a wall 201 of an exhaust passage (e.g., exhaust passage 48). The wall 201 may be a geodetically highest wall of the exhaust passage.

PM sensor assembly 200 is shown from a downstream perspective inside an exhaust passage (e.g., exhaust passage 48 of FIG. 1) such that exhaust gases are flowing from the right hand side of FIG. 2 to the left hand side of FIG. 2 as indicated by arrows. PM sensor assembly 200 may include a cylindrical tube 202 with an inlet 204 on an upstream surface of an extension 208 of the tube 202. The tube 202 is fluidly coupled to the exhaust passage only via the inlet 204, a drainage hole 206, and outlets 224 of a guiding plate 216. Therefore, exhaust gas may only enter or exit the PM sensor assembly 200 via the inlet 204, the drainage hole 206, and outlets 224.

The inlet 204 is substantially normal to and faces the flow of oncoming exhaust gases in the exhaust passage. Thus, the inlet 204 may be in direct contact with exhaust flow, and exhaust gases exiting PF 72 may flow in an unobstructed manner towards the inlet 204 of the PM sensor assembly 200. Further, no components may block or deflect the flow of exhaust gases from the PF 72 to the PM sensor assembly 200. Thus, a portion of exhaust gases for sampling may be conducted via an inlet 204 into PM sensor assembly 200. A remaining portion of exhaust gases in the exhaust passage may flow around an outer body of the PM sensor assembly 200. In this way, the remaining portion of exhaust gases does not flow into the PM sensor assembly. The remaining portion of exhaust gases may be greater in quantity of the portion of exhaust gases flowing into the PM sensor assembly 200. Thus, a quantity of exhaust entering the PM sensor assembly 200 is less than a quantity of exhaust gas flowing around and not entering the PM sensor assembly 200.

The inlet 204 is rectangular and aligned with a vertical axis of the PM sensor assembly 200. The inlet 204 may be located on an extension 208 of the tube 202 and thus is geodetically lower than a perforated plate 216 and a PM sensor 214. In this way, exhaust gas flows up into the tube 202 of the PM sensor assembly 200 in order to be sampled.

The extension 208 may be located at a bottom (e.g., base) of the tube 202 and may resemble a half-cylinder shape. The extension 208 may be located on a downstream half of the tube 202. It will be appreciated by someone skilled in the art that the extension 208 may be other suitable shapes.

A drainage hole 206 is located along the extension 208 downstream of and directly across from the inlet 204. Water droplets and large particulates may form as a result of combustion, which may impinge onto the PM sensor 214 and result in inaccurate soot measurements. The drainage hole 206 is fluidly coupled to the exhaust passage and allows water droplets and large particulates to flow through its circular opening in order to mitigate a quantity of water droplets and large particulates impinging on the PM sensor 214 of the PM sensor assembly. The water droplets and large particulates are less likely to flow up into an outer chamber 210 due to their momentum being greater than a momentum of smaller particulates in the exhaust flow.

As described above, a portion of exhaust gas flowing through the exhaust passage flows into the PM sensor assembly 200 via the inlet 204. A first portion of exhaust gas flowing into the PM sensor assembly 200 flows up along the vertical axis into an outer chamber 210. A second portion of exhaust gas flowing into the PM sensor assembly 200 flows through drainage hole 206. The second portion of exhaust gas may comprise a greater concentration of water droplets and large particulates than the first portion.

The first portion of exhaust gas flowing through the outer chamber 210 may be conducted up toward a top of the tube 202 and down into a central chamber 212. An entrance to the central chamber 212 may be geodetically higher than an entrance to the outer chamber 210. The central chamber 212 and the outer chamber 210 may be parallel and aligned with the vertical axis. Thus, a direction of exhaust flow is inverted from up the vertical axis toward a top of the PM sensor assembly 200 to down toward a bottom of the PM sensor assembly 200 when exhaust flows from the outer chamber 210 to the central chamber 212, respectively. The central chamber 212 may be located between the PM sensor 214 and the guiding plate 216. Exhaust gas may not flow from the outer chamber 210, through the perforated plate 216, and into the central chamber 212. Thus, exhaust gas is conducted up the outer chamber 210 along an entire height of the guiding plate 216 before entering the central chamber 212.

The PM sensor 214 may comprise an upstream surface (also referred to herein as a first surface) and a downstream surface (also referred to herein as a second surface). The first surface of the PM sensor 214 may face a direction of incoming exhaust flow, opposite the guiding plate 216. The second surface of the PM sensor 214 faces a direction opposite of incoming exhaust flow, toward the guiding plate 216. The first surface comprises an electric circuit. The electric circuit may be used to increase a temperature of the PM sensor 214 in response to a particulate load of the PM sensor 214 exceeding a threshold PM sensor load in order to regenerate (e.g., burn off) stored particulate matter.

The second surface comprises a first electrode 220 and a second electrode 222. The first electrode 220 is depicted via solid lines and the second electrode 222 is depicted via small dash lines. As depicted, the first electrode 220 and the second electrode 222 are not electrically coupled to one another. Furthermore, the first electrode 220 and the second electrode 222 may not have equal resistances. As a first example, the first electrode 220 may have a greater resistance than the second electrode 222. As a second example, the second electrode 222 may have a greater resistance than the first electrode 220. Exhaust gas flowing through the central chamber 212 may deposit particulate matter onto the second surface comprising both the first electrode 220 and the second electrode 222. As a quantity of particulate matter on the second surface increases, the first electrode 220 and the second electrode 222 may become bridged (e.g., electrically coupled). Bridged first and second electrodes 220 and 222, respectively, may indicate a PM load of the PM sensor 214 is greater than the threshold PM sensor load and the electric circuit on the first surface may be activated in order to regenerate the PM sensor.

The guiding plate 216 is depicted via medium dash lines and a transparent checkered body. Medium dash lines are greater in length than small dash lines. The guiding plate 216 may guide exhaust gas through the PM sensor assembly 200 in order to evenly distribute particulate matter across the second surface of the PM sensor 214 via surfaces of the guiding plate 216. Surfaces of the guiding plate 216 may also define a passage of the central chamber 212 (e.g., an interior passage). In this way, exhaust gas may flow freely between the central chamber 212 and the guiding plate 216 while depositing soot onto the second surface of the PM sensor 214.

In one example, an exhaust gas flow rate increases as exhaust gas within the guiding plate 216 converges (e.g., flows inward) while the exhaust gas flow rate decreases as exhaust gas within the guiding plate 216 diverges (e.g., flows outward). The guiding plate 216 comprises outlets 224 aligned with the vertical axis on a radius on the tube 202. Exhaust gas flowing down the central chamber 212 may exit the PM sensor assembly 200 only via the outlets 224. As depicted, the outlets 224 are arc-shaped. It will be appreciated by someone skilled in the art that the outlets 224 may be other suitable shapes.

The guiding plate 216 comprises a plurality of concave projections vertically offset from one another. The projections project in a direction away from the PM sensor 214. Surfaces of the projections communicate fluidly with each other and the exhaust passage and may alter an exhaust flow similar to a Galton box (e.g., a quincunx), as will be described below. Openings of the projections may be oblique to the vertical axis. In one example, the openings are exactly 45° to the vertical axis. The guiding plate 216 may alter an exhaust flow such that exhaust flow is promoted to flow toward a bottom portion of the central chamber 212 rather than flowing through the outlets 224 near an upper portion of the guiding plate 216. In this way, particulate matter may be evenly deposited across the second surface of the PM sensor 214 such that bridging of the first and second electrodes 220 and 222, respectively, is equally likely at any position of the second surface.

In the example of FIG. 2, exhaust gas enters the PM sensor assembly 200 via the inlet 204 of the tube 202. The exhaust gas may be conducted upward through the outer chamber 210 before flowing into the central chamber 212. An entrance to the central chamber 212 is located directly above the guiding plate 216. The exhaust gas is then conducted downward toward a bottom of the PM sensor assembly 200 once it enters the central chamber 212 and interacts with both the second surface of the PM sensor 214 and the guiding plate 216. A flow direction of the exhaust gas is altered via the guiding plate 216 as the exhaust gas deposits particulate matter onto the second surface of the PM sensor. As particulate matter is deposited onto the second surface, the first electrode 220 and the second electrode 222 may become bridged (e.g., electrically connected) when a particulate matter load of the PM sensor 214 exceeds a threshold particulate matter load. Furthermore, a resistance of the first electrode 220 or the second electrode 222 is decreased in response to the bridging. As a result, the PM sensor 214 is fully loaded due to particulates leaking from a particulate filter (e.g., PF 72 of FIG. 1) of the exhaust passage. Particulates may be leaking due to the particulate filter being fully loaded or degraded (e.g., cracked). A method for determining the particulate filter being fully loaded or degraded is described below with respect to FIG. 6.

PM sensor assembly 200 may be coupled to exhaust passage 48 (FIG. 1) in a suitable manner such that a top surface of PM sensor assembly 200 is sealed to a wall 201 of the exhaust passage. A top-down view of the PM sensor assembly 200 not being sealed to the wall of the exhaust passage such that components within the PM sensor assembly 200 are visible is shown below in reference to FIG. 3.

Turning now to FIG. 3, a top-down view of a PM sensor assembly 300 detached from a wall of an exhaust passage of a vehicle located on a flat surface is shown. The PM sensor assembly 300 may be used as PM sensor assembly 200 in the embodiment of FIG. 2 or it may be used as exhaust gas sensor 162 of FIG. 1.

The top-down view of the PM sensor assembly 300 depicts a tube 301, a first outer chamber 302, a guiding plate 304, a central chamber 306, a PM sensor 308, and a second outer chamber 310. The first outer chamber 302, the guiding plate 304, the central chamber 306, and the PM sensor 308 may be used as the outer chamber 210, the guiding plate 216, the central chamber 212, and the PM sensor 214 in the embodiment of FIG. 2, respectively. The PM sensor 308 comprises a downstream surface 312, adjacent the central chamber 306 and an upstream surface 314, adjacent the second outer chamber 310. The downstream surface 312 comprises two electrodes indicated by a thick line 316. The upstream surface 314 comprises an electric circuit indicated by a thick line 318.

As described above, exhaust gas is conducted up the first outer chamber 302 before flowing into the central chamber 306. The guiding plate 304 hermetically seals the first outer chamber 302 from the central chamber 306 for a first portion of the tube 301. Exhaust gas may exit the first outer chamber 302 and flow into the central chamber 306 via an opening located directly above the guiding plate 304. In this way, exhaust gas flows up an entire height of the guiding plate 304 before flowing through the opening to the central chamber 306.

The central chamber 306 is located in a space between the guiding plate 304 and the PM sensor 308. A width 320 of the space may be between 1-5 millimeters. In one example, the width 320 is exactly 1.5 millimeters. In other embodiments, the width 320 may be less than 1 millimeter or greater than 5 millimeters.

Exhaust in the central chamber 306 flows down toward a bottom of the tube 301 in a direction opposite the flow of exhaust in the first outer chamber 302. Exhaust in the central chamber 306 flows into and between the guiding plate 304 and the downstream surface 312 of the PM sensor 308. The downstream surface 312 may be composed of a material capable of receiving and storing particulate matter while also being able to withstand high temperatures. In one example, the PM sensor 308 may be ceramic. The first and second electrodes of the downstream surface 312 may become bridged as particulate matter (e.g., soot) is deposited onto the downstream surface 312 of the PM sensor 308. The guiding plate 304 may comprise a material unable to store particulate matter while coming into contact with and guiding the exhaust flow in the central chamber 306. In one example, the guiding plate 304 may be plastic (e.g., polyurethane).

The upstream surface 314 of the PM sensor 308 comprising the electric circuit may be activated in response to the first and second electrodes of the downstream surface 312 bridging. Activating the electric circuit may include flowing electricity through the electric circuit in order to heat the PM sensor 308 and regenerate the particulate matter stored on the downstream surface 312. The downstream surface 312 may be regenerated (e.g., the electric circuit remains active) until the first and second electrodes are no longer bridged. In another example, additionally or alternatively, the electric circuit may remain active for a threshold duration of time (e.g., 20 seconds). Regenerated particulate matter (e.g., ash) may fall into the central chamber 306 and swept away by incoming exhaust gas.

As described above, the guiding plate 304 comprises a plurality of concave projections vertically offset and in fluid communication with each other. The guiding plate 304 may promote exhaust gas in the central chamber 306 to flow in a downward motion toward the bottom (e.g., a base) of the tube 301. Furthermore, the guiding plate 304 may be in fluid communication with an exhaust passage at an interface between the guiding plate 304 and an outer radius of the tube 301 along a central axis 322 of the PM sensor assembly 300. As an example, the guiding plate 304 comprises outlets along a body of the tube 301 such that exhaust near the interface may flow out of the tube 301 and into the exhaust passage. In this way, exhaust gas may be equally promoted to flow out of the tube 301 along a periphery of the guiding plate 304, and therefore near a periphery of the PM sensor 308, while also flowing down the central chamber 306 in order to reach the base of the tube 301. By doing this, soot may be evenly deposited onto the downstream surface 312 comprising the first and second electrodes.

Exhaust gas in the central chamber 306 flows in a substantially downward direction. Exhaust gas in the central chamber 306 cannot flow into the second outer chamber 310 due to the physically coupling between the PM sensor 308 and the tube 301. In this way, the second outer chamber 310 does not receive exhaust gas and is not fluidly coupled to the exhaust passage, the first outer chamber 302, and/or the central chamber 306. The tube 301 is sealed at the base such that exhaust gas flowing out of the tube 301 does not flow into a path of an inlet (e.g., inlet 204) of the tube 301

In the example of FIG. 3, the PM sensor assembly 300 comprises the guiding plate 304 located along its center and spaced away from the PM sensor 308. The PM sensor 308 is located upstream of the guiding plate 304. Three chambers are located within the PM sensor assembly including the first outer chamber 302, the central chamber 306, and the second outer chamber 310. The first outer chamber 302 and the second central chamber 306 are fluidly coupled and sandwich the guiding plate 304. The second outer chamber is located upstream of the PM sensor 308 and does not receive exhaust gas. Exhaust gas in the central chamber 306 flows into the guiding plate 304 and the PM sensor 308. The exhaust gas in the central chamber 306 may flow out of the PM sensor assembly 300 via exits located at the interface between the guiding plate 304 and the tube 301 before or after depositing particulate matter onto the PM sensor.

The guiding plate 304 comprises a plurality of concave projections which may guide an exhaust flow in the central chamber 306 in order to more evenly distribute exhaust flow across the downstream surface 312 of the PM sensor 308. The concave projections will be elaborated below in reference to FIG. 4.

Turning now to FIG. 4, a face-on view of a guiding plate 400 from a downstream to upstream direction is depicted. In the present example, the guiding plate 400 is in front of and blocks a view of a central chamber and a PM sensor. The guiding plate 400 may be used as the guiding plate 304 in the embodiment of FIG. 3 or as the guiding plate 216 in the embodiment of FIG. 2.

The guiding plate 400 may comprise a plurality of projections 402. The projections 402 are physically coupled to adjacent projections 402 such that each side of the projections 402 is physically coupled to another side of a corresponding adjacent projection of the projections 402. A close-up view 403 depicts a detailed structure of a single projection 410.

As depicted, projection 410 comprises four legs A, B, C, and D. Legs A, B, C, and D, correspond to legs A, B, C, and D of a dash circled projection of the projections 402 located on the guiding plate 400. Legs A, B, C, and D are physically coupled to other legs of adjacent projections of the projections 402. In one example, leg A of projection 410 is physically coupled to legs of three adjacent projections 402. Likewise, legs B, C, and D of projection 410 are each physically coupled to legs of three corresponding adjacent projections of the projections 402. An area between the legs A, B, C, and D is open to the central chamber such that exhaust gas may flow freely between the guiding plate 400 and the central chamber.

As depicted, projection 410, and thus projection 402, are concave. A cross-section of the projection 410 may be "U-shaped." It will be appreciated by someone skilled in the art that the projections 402 may be other suitable concave shapes (e.g., parabolic, V shaped, saddle, cup, etc.).

Projections 402 are hermetically sealed along the legs and opening arches 412 such that gas in the central chamber may not flow through the guiding plate 400 and into an outer chamber (e.g., the first outer chamber 302) or vice-versa.

Opening arches 412 are located between each of the legs A, B, C, and D. The opening arches 412 are physically coupled to opening arches of other adjacent projections. For example, one of the opening arches 412 of the projection 410 may by physically coupled to a single opening arch of an adjacent projection of the projections 402. In this way, the projection 410 may be coupled to a total of twelve adjacent legs and four opening arches of the adjacent projections. Furthermore, the projections 402 are physically coupled to one another obliquely to the vertical and/or horizontal axes. In this way, a pattern of the projections 402 on the guiding plate 400 may be a zig-zag.

Projections 402 located along a top side 404 of a tube (e.g., tube 301) of the guiding plate 400 may be cut in half along the horizontal axis and open to incoming gas. For example, gas flowing from an outer chamber (e.g., outer chamber 302) may flow into a central chamber (e.g., central chamber 306) and or the guiding plate 400 via the projections located adjacent to the top side 404 of the projections 402. Gas in the central chamber and the guiding plate 400 may flow back and forth between or remain in the central chamber and the guiding plate 400, respectively. As will be described below, exhaust gas flowing through the projections 402 of the guiding plate 400 may flow in a zig-zag direction, similar to a Galton box.

Exhaust gas flowing through the projections 402 of the guiding plate 400 may flow out of the tube via projections 402 located adjacent side 406A or side 406B. Projections 402 located near side 406A or side 406B may be cut in half along the vertical axis and are in fluid communication with an exhaust passage. In this way, the guiding plate 400 comprises a plurality of outlets located along the sides 406A and 406B.

Exhaust gas may flow to a base 408 of the guiding plate 400. The base of the guiding plate 400 may also be a base of the tube (e.g., the base of the tube is base 408). Thus, the base 408 is hermetically sealed from the exhaust passage such that gas flowing through the guiding plate 400 may not flow through the base 408. Said another way, the base 408 does not comprise outlets and is not fluidly coupled to the exhaust passage. In this way, gas flowing toward the base 408 may ricochet off the base 408 and flow toward outlets located at either side 406A or side 406B.

The example of FIG. 4 illustrates the guiding plate 400 with a plurality of projections 402 physically coupled to one another such that exhaust gas in the central chamber may not flow through the guiding plate 400 and into the outer chamber. The projections 402 are in fluid communication with each other and may alter an exhaust flow substantially similar to a Galton box in order to more evenly distribute exhaust flow across a face of a PM sensor. The flow of exhaust through the guiding plate 400 will be described in greater detail below with reference to FIG. 5.

Turning now to FIG. 5A, a guiding plate 500 comprising a plurality of projections 502 altering an example exhaust flow is shown. The guiding plate 500 and the projections 502 may be used as guiding plate 400 and projections 402 in the embodiment of FIG. 4. The guiding plate 500 and the projections 502 are depicted via medium dashed lines.

A first example exhaust flow 504 is depicted via thick, large dashed lines. A second example exhaust flow 506 is depicted via thick, small dashed lines. Large dashed lines are longer than medium and small dashed lines. Medium dashed lines are longer than small dashed lines. A third example exhaust flow 508 is depicted via thick, dashed two dot lines. The third example flow 508 originates from a substantially similar location as the first example flow 504 in the present example. A fourth example exhaust flow 510 is depicted via thick, dashed single dot lines. It will be appreciated by someone skilled in the art that many different exhaust flow patterns may occur in the guiding plate 500 and that the guiding plate 500 is not limited to the examples described below.

The projections 502 of the guiding plate 500 adjacent a top-side 512 of the guiding plate 500 may serve as inlets and allow exhaust gas to enter a flow path of the guiding plate 500. Therefore, the first, second, third, and fourth example flows 504, 506, 508, and 510, respectively, may enter the guiding plate 500 via the projections 502 adjacent the top-side 512. Exhaust gas may enter the guiding plate 500 in a direction parallel with a central axis 501. Exhaust gas flowing through projections 502 may exit the guiding plate 500, and a PM sensor assembly (e.g., particulate matter sensor assembly 200) via projections 502 located adjacent to sides 514A or 514B. In this way, projections 504 located adjacent sides 514A or 514B may be used as outlets.

The first example exhaust flow 504 enters the guiding plate 500 near the side 514A. The first example exhaust flow 504 is substantially linear and parallel to the central axis 501. The first example exhaust flow 504 flows out of the guiding plate 500, and therefore out of the PM sensor assembly and into an exhaust passage before reaching a base 516 of the guiding plate 500. As described above, the base 516 of the guiding plate 500 is sealed such that exhaust gas may not flow through the base 516.

The second example exhaust flow 506 enters the guiding plate 500 near the side 514B. The second example exhaust flow 506 flows obliquely to the central axis 501 such that it exits the guiding plate 500 along the side 514A. In this way, the second sample exhaust flow 506 traverses an entire width of the guiding plate 500 before exiting the guiding plate 500 along the side 514A and entering the exhaust passage housing the PM sensor assembly.

The third example exhaust flow 508 enters the guiding plate 500 near the side 514A. The third example exhaust flow 508 flows to and away from the side 514B before exiting the side 514B near the base 516. Portions of the third example exhaust flow 508 zig-zag such that a direction of the exhaust flow in a current projection of the projections 502 is perpendicular to a direction of exhaust flow in a previous projection of the projections 502.

For example, an exhaust flow may flow through a plurality of projections 502 in a direction oblique to or parallel to the central axis 501. Exhaust flow flowing from a first of the projections 502 to a second of the projections 502 may flow parallel to, oblique to, or perpendicular to an initial flow based on a location of the second of the projections 502 relative to the first of the projections 502. The direction of exhaust flow may also be based on exhaust flows in a same projection of the projections 502 colliding. For example, exhaust flows in the projections 502 of the guiding plate 500 may collide and mix, thereby altering a direction of the exhaust flows.

The fourth example exhaust flow 510 enters the guiding plate 500 along the central axis 501. The fourth example exhaust flow 510 flows parallel to the central axis 501 in a zig-zag motion. The fourth example exhaust flow 510 collides with the base 516 and begins to flow toward the side 514A. The fourth example exhaust flow 510 flows out the side 514A at a location substantially similar to the outflow of the first example exhaust flow 504.

Turning now to FIG. 5B, a portion of the projections 540 with exhaust gas flowing through passages within the projections 540 is shown. Projections 540 may be used as a portion of the projections 502 of FIG. 5A.

In one example, an exhaust flow rate through the projections 540 may be increased as exhaust flow is directed toward a central axis 541 of the projections 540. Additionally or alternatively, the exhaust flow rate through the projections 540 may be decreased as exhaust flow is directed away from the central axis 541.

Exhaust flows 550 and 552 enter a projection 551 of the projections 540 from different angles. Exhaust flow 550 enters the projection 551 from a pathway farther away from the central axis 541 than the exhaust flow 552. Exhaust flows 550 and 552 converge within the projection 551 before flowing to an end of the projection 551. In this way, exhaust flow 550 begins to flow toward the central axis 501 after it enters the projection 551 and exhaust flow 552 begins to flow away from the central axis 501 as it enters the projection 551 (e.g., the exhaust flows 550 and 552 may be oblique to or perpendicular to each other). The exhaust flows may divide and flow into two adjacent projections 559 and 563 geodetically lower than and in fluid communication with the projection 551. Flow rates of the exhaust flows 550 and 552 may be increased as they converge (e.g., merge) within the projection 551.

A portion of the converged exhaust (e.g., exhaust flow 558) flows into the projection 559 while a remaining portion of the converged exhaust (e.g., exhaust flow 560) flows into the projection 563. In this way, exhaust in the projection 551 may be divided upstream of the projections 559 and 563. In one example, the exhaust flow 560 may be greater in volume than the exhaust flow 558.

Exhaust flows 554 and 556 enter a projection 555 from different angles. Exhaust flow 554 flows away from the central axis 501 as it enters the projection 555 while exhaust flow 556 flows toward the central axis 501 as it enters the projection 555. A flow rate of the exhaust flows 554 and 556 may increase as the exhaust flows converge within the projection 555.

A portion of the converged exhaust (e.g., exhaust flow 562) flows into the projection 563 and combines (e.g., converges) with exhaust flow 560. A remaining portion (e.g., exhaust flow 564) of the converged exhaust flow in the projection 555 flows into the projection 567. Exhaust flow 562 may have a greater volume of exhaust than exhaust flow 564. In this way, the combined exhaust flow of the exhaust flows 560 and 562 may have a flow rate greater than a flow rate of either the exhaust flow 558 in the projection 559 or the exhaust flow 564 in the projection 567.

Turning now to FIG. 6, a method 600 for determining a particulate load of a PM sensor assembly being greater than a threshold particulate load in order to regenerate the PM sensor is depicted. The method 600 may further depict degradation of a particulate filter in an exhaust passage is degraded based on a time interval between PM sensor regeneration being less than a threshold time interval. Instructions for carrying out method 600 may be executed by a controller (e.g., controller 12 shown in FIG. 1) based on instructions stored on a memory of the controller and in conjunction with signals received from sensors of the engine system, such as the sensors described above with reference to FIGS. 1 and 2. The controller may employ engine actuators of the engine system to adjust engine operation, according to the methods described below.

Method 600 may be described in reference to components depicted in FIGS. 1, 2, and 3. Specifically, the method 600 may the controller 12, the PF 72, the exhaust gas sensor 162, the PM sensor assembly 200, the PM sensor 214, the first and second electrodes 220 and 222, and the guiding plate 216 with reference to FIGS. 1 and 2, respectively.

Method 600 being at 602 to determine, estimate, and/or measure current engine operating parameters. Current engine operating parameters may include but are not limited to engine load, engine speed, vehicle speed, manifold vacuum, throttle position, exhaust pressure, and an air/fuel ratio.

At 604, the method 600 includes measuring an electrical resistance of the first and second electrodes located on a downstream surface of the PM sensor within the PM sensor assembly. In the embodiment of FIG. 6, the first electrode may have a greater resistance than the second electrode. However, it will be appreciated by someone skilled in the art that the second electrode may have a greater resistance than the first electrode.

At 606, the method 600 includes determining if the electrodes are electrically connected (e.g., bridged). The electrodes may become bridged as soot is deposited onto the downstream surface of the PM sensor by exhaust flowing freely between a central chamber and a guiding plate. As the soot builds up between the first and second electrodes, the soot may touch both electrodes simultaneously and as a result, the electrodes are bridged. When the electrodes are bridged, the resistance of the first electrode may decrease to a resistance of the second electrode due to the conductivity of the soot. If the resistance of the first electrode is greater than the resistance of the second electrode, then the electrodes are not bridged and the method 600 proceeds to 608 to maintain current engine operating parameters and to not regenerate the PM sensor in the PM assembly. Furthermore, a particulate filter (PF) in an exhaust passage may not be leaking or fully loaded with PM (e.g., a PF PM load is less than a threshold PF PM load). Thus, the PF in the exhaust passage is not regenerated.

If the resistance of the first electrode is substantially equal to the resistance of the second electrode, then the electrodes are bridged and the method 600 proceeds to 610 to activate an electric circuit of the PM sensor in order to regenerate the PM sensor. The electric circuit may be electrically connected to one or more of the first and second electrodes. Thus, the electric circuit may be activated by one or more of the first and second electrodes in response to the first and second electrodes being bridged. Alternatively, the electric circuit may be activated (e.g., switched on) via the controller in response to determining that the first and second electrodes are bridged. The controller may further adjust actuators of the engine in response to activating the electric circuit. For example, the controller may adjust an engine operation in order to regenerate the particulate filter located in the exhaust passage. The adjustments may include retarding spark, decreasing an air/fuel ratio of one or more cylinders, increasing the air/fuel ratio of one or more cylinders, and/or increasing a post-injection volume. In this way, regeneration of the PM sensor of the PM sensor assembly may trigger a regeneration of the PF located in the exhaust passage based on the first and second electrodes being bridged.

At 612, the method 600 includes disabling the PM sensor regeneration in response to the first and second electrodes no longer being bridged. The first and second electrodes may no longer be bridged after the electric circuit regenerates the PM sensor and thus, burns off at least a portion of accumulated soot on the PM sensor. By burning off the soot, the bridge between the first and second electrodes may also be burned and the resistance of the first electrode may become greater than the resistance of the second electrode. The controller may deactivate the electric circuit in response to determining the resistance of the first electrode is greater than the resistance of the second electrode. Alternatively, the first and second electrodes may be electrically coupled to the electric circuit and the circuit may be deactivated by the first and second electrodes in response to the electrodes no longer being bridged.

The regeneration of the PF in the exhaust passage may also be terminated in response to deactivating the electric circuit. The controller may adjust engine operation back to an optimal engine operation based on a current engine load. Thus, a duration of regeneration for the PM sensor and the PF are substantially equal. Additionally or alternatively, the regeneration of the PF in the exhaust passage may be terminated after a threshold duration has passed after termination of the electric circuit. For example, the electric circuit is deactivated and then after the threshold duration has passed, the controller signals actuators of the engine to return to a nominal operation in order to deactivate PF regeneration.

In one example, additionally or alternatively, the regeneration of the PF sensor and the regeneration of the PF may operate for lengths of a first threshold and a second threshold, respectively. In this way, lengths of regeneration of the PF sensor and the PF may be independent. In other words, the first threshold may not be equal to the second threshold. In one embodiment, the first threshold may be less than the second threshold (e.g., the PF is regenerated for a greater length of time compared to the PM sensor). In another embodiment, the first threshold may be greater than the second threshold (e.g., the PF sensor is regenerated for a greater amount of time than the PF).

At 614, the method includes determining a time interval between a last regeneration and a current regeneration of the PM sensor. The last regeneration is defined as a regeneration event that occurred directly before a current regeneration event. The time interval may be calculated based on a duration of time between initiation of the last regeneration and initiation of the current regeneration (e.g., 120 minutes). A time interval may be less than a previous time interval as the PF in the exhaust passage (e.g., particulate filter 72 of FIG. 1) becomes degraded and captures less soot. For example, the particulate filter develops leaks (e.g., cracks), which may allow a greater amount of soot to flow to the PF sensor, resulting in more frequent regenerations of the PF sensor.

At 616, the method 600 determines if the measured time interval is less than a threshold time interval. The threshold time interval may be based on a set threshold (e.g., 200 minutes), a last time interval measured, or a percentage of the last time interval measured (e.g., 50% of the last time interval). Further, the threshold time interval may be based on a threshold that indicates that the time interval is decreasing and the PF sensor has to be regenerated at an increasing rate. Additionally or alternatively, the threshold time interval may be adjusted based on engine operating parameters. For example, the threshold time interval may be decreased as an engine load increases.

If the time interval is not less than the threshold time interval, then the method 600 proceeds to 608 to maintain current engine operation and continue monitoring the electrodes of the PM sensor.

If the time interval is less than the threshold time interval, then the method 600 proceeds to 618 to indicate the PF of the exhaust passage, upstream of the PM sensor assembly, is leaking. Indication of the PF leaking includes adjusting an engine operation and activating an indicator lamp 620 (e.g., in order to indicate to a vehicle operator that the PF is degraded and needs to be replaced).

As an example, a controller (e.g., controller 12) may signal various actuators of an engine (e.g., throttle 62 of engine 10) to limit a torque output of the engine in order to reduce exhaust produced to meet emissions standards. As another example, additionally or alternatively, the method 600 may advance one or more of a spark timing and fuel injection, increase air/fuel ratio, and/or increase EGR. By increasing EGR flow to one or more cylinders of the engine, a combustion mixture temperature(s) is decreased and a volume of fuel injection may be decreased. By doing this, an amount of soot being exhausted from one or more cylinders of the engine may be decreased.

Thus, the method of FIG. 6 provides a method comprising diverting exhaust gas from an exhaust pipe to a PM sensor assembly, where the PM sensor assembly includes a PM sensor with electrodes on a downstream surface and an electric circuit on an upstream surface. The method includes adjusting engine operation based on electrodes of the PM sensor being bridged (e.g., connected). The bridging is based on resistances of the electrodes becoming substantially equal.

In this way, a PM sensor assembly may receive a sample exhaust flow from an exhaust passage in order to determine a PM load of a PF in the exhaust passage. PM from the exhaust accumulates onto a surface of a PM sensor located within the PM sensor assembly in order to signal a regeneration and/or degradation of the PF. Exhaust gas in the PM sensor assembly is evenly distributed across the surface of the PM sensor via a guiding plate. The technical effect of using a guiding plate to evenly distribute a sample exhaust flow across a surface of a PM sensor is to increase a uniformity of PM being deposited onto the surface of the PM sensor. By doing this, an accuracy of a determination of a PF being fully loaded and/or degraded is increased.

In a first example, a system comprises a tube positioned in an exhaust passage of an engine where a particulate matter sensor is positioned within the tube and a flow guiding plate is also positioned within the tube and substantially parallel to a vertical axis of the tube. The guiding plate has a plurality of projections with surfaces of the projections defining an interior passage in proximity to the particulate matter sensor, the surfaces of the projections directing flow against the particulate matter sensor.

In a first embodiment of the first example, the system further comprises an inlet of the tube aligned with the vertical axis of the tube, and where the tube further comprises a drainage hole spaced away from the inlet, where both the drainage hole and the inlet fluidly connect an interior of the tube with the exhaust passage.

In a second embodiment, which may additionally include the first embodiment, the system of the first example additionally or alternatively includes the particulate matter sensor having a switchable electrical circuit on a first surface facing away from the guiding plate in the tube.

In a third embodiment, which may include one or more of the first and second embodiments, the system of the first example further includes the particulate matter sensor has two, unconnected electrodes on a second surface facing the guiding plate.

In a fourth embodiment, which may include one or more of the first through third embodiments, the system of the first example further comprising a central chamber aligned with a vertical axis of the tube and located between the guiding plate and the second surface of the particulate matter sensor.

In a fifth embodiment, which may include one or more of the first through fourth embodiments, the system of the first example further comprising where the plurality of outlets are located along an interface between the guiding plate and the tube.

In a sixth embodiment, which may include one or more of the first through fifth embodiments, the system of the first example further comprising where exhaust gas flows in the tube in a direction perpendicular or oblique to a direction of exhaust flow in the exhaust passage.

In a seventh embodiment, which may include one or more of the first through the sixth embodiments, the system of the first example further comprising where the projections of the guiding plate are concave and physically coupled to and in fluid communication with adjacent projections.

In a second example, a method comprising conducting a portion of exhaust gas from an engine through an opening in a tube into an outer chamber within the tube, guiding the portion of exhaust gas from the outer chamber into a central chamber located between a particulate matter sensor and a guiding plate both of which are positioned within the tube, and flowing part of the portion of the exhaust gas entering the central chamber through concave projections of the guiding plate and onto a surface of the particulate matter sensor.

In a first embodiment of the second example, the method further includes flowing the portion of exhaust gas onto a surface of the particulate matter sensor further comprises flowing the portion of exhaust gases onto one of a pair of separated electrodes located on the surface of the particulate matter sensor.

In a second embodiment of the first example, which may additionally or alternatively include the first embodiment, the method further includes where the separate electrodes are electrically coupled when a load of particulate matter from the portion of the exhaust flowing on to the separated electrode exceeds a threshold particulate matter load.

In a third embodiment, which may additionally or alternatively include one or more of the first and second embodiments, the method further includes where a resistance of the separate electrode decreases in response to electrically coupling the separate electrodes.

In a third example, a system comprises a tube positioned in an exhaust passage of an engine, a particulate matter sensor and a guiding plate positioned in the tube. The guiding plate comprises a plurality of concave projections extending away from the guiding plate, and where surfaces of the concave projections define a central chamber and are in fluid communication with each other and the exhaust passage. The particulate matter sensor comprises an upstream surface with an electric circuit and a downstream surface with separate first and second electrodes, the upstream surface communicating with the central chamber and receiving a portion of the exhaust flow which is directed onto the upstream surface by the concave projections. The system further comprises a controller with computer-readable instructions for determining when a load of particulate matter in the exhaust which is collected on the upstream surface of the sensor exceeds a threshold particulate matter load and initiating a regeneration of the particulate matter sensor.

A first embodiment of the third example, where regenerating a particulate matter filter positioned in the engine exhaust based on how frequently the particulate matter sensor is regenerated.

A second embodiment of the third example, which may additionally or alternatively include the first example, the system further comprising the particulate matter sensor, the guiding plate, and the central chamber located therebetween are in fluid communication.

A third embodiment of the third example, which may additionally or alternatively include one or more of the first and second embodiments, the system further includes where an exhaust gas sample flows freely between the particulate matter sensor, the guiding plate, and the central chamber.

A fourth embodiment of the third example, which may additionally or alternatively include one or more of the first through third embodiments, the system further includes where the guiding plate redirects exhaust flow similar to a quincunx.

A fifth embodiment of the third example, which may additionally or alternatively include one or more of the first through fourth embodiments, the system further includes where the tube and the guiding plate are hermetically sealed at a shared base.

A sixth embodiment of the third example, which may additionally or alternatively include one or more of the first through fifth embodiments, the system further includes where the tube comprises an inlet upstream of and larger than a drainage opening of the tube.

A seventh embodiment of the third example, which may additionally or alternatively include one or more of the first through sixth embodiments, the system further includes where the particulate matter sensing element is downstream of a particulate matter filter of the exhaust passage.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A system comprising:
a tube positioned in an exhaust passage of an engine;
a particulate matter sensor positioned within the tube; and
a flow guiding plate positioned within the tube parallel to a vertical axis of the tube and having a plurality of projections with surfaces of the projections defining an interior passage in downstream to the particulate matter sensor, the surfaces of the projections directing flow against the particulate matter sensor;
an extension having a half-cylinder shape located on a downstream half and bottom of the tube; and
wherein the extension comprises a rectangular inlet on an upstream surface of the extension and aligned with a vertical axis of the particulate sensor, and a drainage hole on a downstream surface of the extension directly across from the inlet,
wherein the projections are concave and project away from the particulate matter sensor in a direction opposite to a direction of incoming exhaust flow.

2. The system of claim 1, wherein the particulate matter sensor has a switchable electrical circuit on a first surface facing away from the guiding plate in the tube.

3. The system of claim 1, wherein the particulate matter sensor has two, unconnected electrodes on a second surface facing the guiding plate.

4. The system of claim 3, further comprising a central chamber aligned with the vertical axis of the tube and located between the guiding plate and the second surface of the particulate matter sensor.

5. The system of claim 1, wherein a plurality of outlets are located along an interface between the guiding plate and the tube.

6. The system of claim 1, wherein exhaust gas flows in the tube in a direction perpendicular or oblique to a direction of exhaust flow in the exhaust passage.

7. The system of claim 1, wherein the projections of the guiding plate are physically coupled to and in fluid communication with adjacent projections.

8. A method, comprising:
conducting a portion of exhaust gas from an engine through an extension in a tube into an outer chamber within the tube;
guiding the portion of exhaust gas from the outer chamber into a central chamber located between a particulate matter sensor and a guiding plate both of which are vertically aligned with a vertical axis of the tube; and
flowing part of the portion of the exhaust gas entering the central chamber through concave projections of the guiding plate and onto a surface of the particulate matter sensor, wherein the projections project away from the particulate matter sensor in a direction opposite to a direction of incoming exhaust flow,
wherein the extension having a half-cylinder shape located on a downstream half and bottom of the tube; and
wherein the extension comprises a rectangular inlet on an upstream surface of the extension and aligned with a vertical axis of the particulate sensor, and a drainage hole on a downstream surface of the extension directly across from the inlet.

9. The method of claim 8, wherein flowing the part of the portion of exhaust gas onto a surface of the particulate matter sensor further comprises flowing the part of the portion of exhaust gas onto one of a pair of separated electrodes located on the surface of the particulate matter sensor.

10. The method of claim 9, wherein the separated electrodes are electrically coupled when a load of particulate matter from the part of the portion of the exhaust gas flowing onto the separated electrodes exceeds a threshold particulate matter load.

11. The method of claim 10, wherein a resistance of the separated electrodes decreases in response to electrically coupling the separated electrodes.

12. A system, comprising:
a tube positioned in an exhaust passage of an engine;
a particulate matter sensor positioned in the tube;
a guiding plate positioned in the tube,
the guiding plate comprising a plurality of concave projections extending away from the guiding plate and away from the particulate matter sensor, in a direction opposite to a direction of incoming exhaust flow, and where surfaces of the concave projections define a central chamber and are in fluid communication with each other and the exhaust passage;
the particulate matter sensor comprising an upstream surface with an electric circuit and a downstream surface with separate first and second electrodes, the upstream surface communicating with the central chamber and receiving a portion of the exhaust flow which is directed onto the upstream surface by the concave projections;
an extension having a half-cylinder shape located on a downstream half and bottom of the tube; wherein the extension comprises a rectangular inlet on an upstream surface of the extension and aligned with a vertical axis of the particulate sensor, and a drainage hole on a downstream surface of the extension directly across from the inlet; and
a controller with computer-readable instructions for:
determining when a load of particulate matter in the exhaust which is collected on the upstream surface of the sensor exceeds a threshold particulate matter load and initiating a regeneration of the particulate matter sensor.

13. The system of claim 12, further comprising regenerating a particulate matter filter positioned in an engine exhaust based on how frequently the particulate matter sensor is regenerated.

14. The system of claim 12, wherein the particulate matter sensor, the guiding plate, and the central chamber located therebetween are in fluid communication.

15. The system of claim 14, wherein an exhaust gas sample flows freely between the particulate matter sensor, the guiding plate, and the central chamber.

16. The system of claim 12, wherein the guiding plate redirects exhaust flow in a zig-zag direction.

17. The system of claim 12, wherein the tube and the guiding plate are hermetically sealed at a shared base.

18. The system of claim 12, wherein the particulate matter sensor is downstream of a particulate matter filter of the exhaust passage.

* * * * *